United States Patent [19]
Schmidhauser

[11] Patent Number: 5,344,999
[45] Date of Patent: Sep. 6, 1994

[54] 1,3-BIS(4-HYDROXYPHENYL)-1,3-DIALKYL-CYCLOHEXANES AND POLYCARBONATES PREPARED THEREFROM

[75] Inventor: John C. Schmidhauser, Schenectady, N.Y.

[73] Assignee: General Electric Company, Schenectady, N.Y.

[21] Appl. No.: 130,500

[22] Filed: Oct. 1, 1993

Related U.S. Application Data

[62] Division of Ser. No. 989,309, Dec. 11, 1992, Pat. No. 5,281,688.

[51] Int. Cl.$^5$ .............................................. C07C 39/17
[52] U.S. Cl. ..................................................... 568/721
[58] Field of Search ................................. 568/718, 721

[56] References Cited

U.S. PATENT DOCUMENTS

| | | |
|---|---|---|
| 3,326,855 | 6/1967 | Matzner et al. ........................ 568/721 |
| 3,395,186 | 9/1968 | Matzner et al. ........................ 568/721 |
| 3,408,407 | 10/1968 | Cotter . | 
| 5,281,688 | 1/1994 | Schmidhauser ....................... 528/196 |

FOREIGN PATENT DOCUMENTS

| | | | |
|---|---|---|---|
| 3298 | 2/1968 | Japan .................................... 568/721 |
| 6513720 | 4/1967 | Netherlands ......................... 568/721 |

OTHER PUBLICATIONS

Sumitomo, Chemical Abstract vol. 98 p. 1605v Jan. 17, 1983.

*Primary Examiner*—Werren B. Lone
*Attorney, Agent, or Firm*—William H. Pittman

[57] ABSTRACT

1,3-Bis(4-hydroxyphenyl)-1,3-dialkylcyclohexanes, as illustrated by 1,3-bis(4-hydroxyphenyl)-1, 3-dimethylcyclohexane, may be prepared by the reaction of phenol with a 1,5-dialkyl-1,4-cyclohexadiene under acidic conditions. Polycarbonates prepared therefrom have high glass transition temperatures and are expected to be ductile.

4 Claims, No Drawings

1,3-BIS(4-HYDROXYPHENYL)-1,3-DIALKYLCYCLOHEXANES AND POLYCARBONATES PREPARED THEREFROM

This application is a division of application Ser. No. 07/989,309, filed Dec. 11, 1992. Now U.S. Pat. No. 5,281,688.

This invention relates to new compositions of matter, and more particularly to new polycarbonates and precursors thereof.

Polycarbonates are a class of high performance engineering resins characterized by optical clarity, high ductility and other advantageous properties. They are frequently employed as lenses and windows by reason of their transparency. Bisphenol A polycarbonate is the principal commercial available resin of this type. It is derived from 2,2-bis(4-hydroxyphenyl)propane, and typically has a glass transition temperature of about 150° C.

It is of increasing interest to prepare polycarbonates which, while retaining the ductility of bisphenol A polycarbonates, have higher glass transition temperatures and are therefore more resistant to softening when heated. Typical areas of application of such polycarbonates are in the preparation of automotive headlamp lenses, which are becoming smaller in size and therefore characterized by closer proximity of the lens to the heat-generating light source, and in windows for aircraft operating at high altitudes, wherein solar heating effects may be pronounced.

The present invention provides a class of polycarbonates which have glass transition temperatures typically 10°–45° C. higher than those of bisphenol A polycarbonates, and which are expected to be ductile. Also provided is a series of bisphenols convertible to said polycarbonates.

In one of its aspects, the invention includes 1,3-bis(4-hydroxyphenyl)-1,3-dialkylcyclohexanes (hereinafter sometimes simply "cyclohexane bisphenols") of the formula

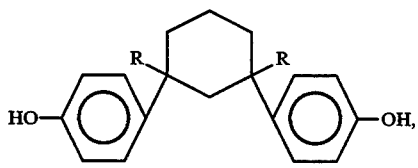

wherein R is a $C_{1-4}$ primary alkyl radical. Thus, the R radicals may each be methyl, ethyl, propyl, 1-butyl or 2-methylpropyl. Methyl radicals are preferred.

The cyclohexane bisphenols of this invention are distinguishable from the bis(4-hydroxyphenyl)-1,4-dimethylcyclohexanes of U.S. Pat. No. 3,395,186 and the 1,4-bis(4-hydroxyphenyl)cyclohexane of U.S. Pat. No. 3,408,407 in that the former lack the benzhydryl groups present in the latter. Benzhydryl groups (i.e., C—H moieties attached to a benzene ring) are subject to thermal and oxidative attack and therefore detract from the stability of bisphenols and polycarbonates containing them.

The cyclohexane bisphenols of the invention may be prepared by the reaction of phenol with a corresponding 1,5-dialkyl-1,4-cyclohexadiene under acidic conditions. Said reaction preferably takes place in the presence of a catalytic amount of a mercaptan as promoter.

This reaction produces the cis- and trans-configured isomers of the cyclohexane bisphenol. Said isomers have the following structures, respectively:

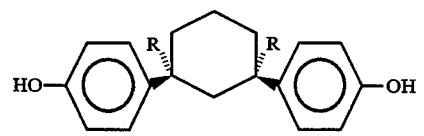

and

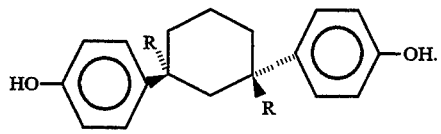

The cis- and trans-isomers may be separated by fractional crystallization or by flash column chromatography, typically using a mixture of ethyl acetate and hexane as the eluent.

The preparation of the cyclohexane bisphenols of this invention is illustrated by the following example. Molecular structures were confirmed by proton and carbon-13 nuclear magnetic resonance spectroscopy.

EXAMPLE 1

A mixture of 270 grams (2850 mmol.) of phenol and 3 ml. of dodecylthiol was heated to 50° C. and hydrogen chloride gas was passed into it for 30 minutes. Starting at 15 minutes, 30 grams (277.7 mmol.) of 1,5-dimethyl-1,4-cyclohexadiene was added over 8 minutes. Stirring at 50° C. was continued for 22 hours, after which the mixture was diluted with ethyl acetate, washed three times with water and once with saturated sodium chloride solution, dried over magnesium sulfate and vacuum stripped to remove excess phenol. The brown residue was recrystallized from chlorobenzene to yield a 70:30 (by weight) mixture of the trans- and cis-isomers of 1,3-bis(4-hydroxyphenyl)-1,3-dimethylcyclohexane. The yield was 25 grams, or 32% of theoretical.

The trans- and cis-isomers were separated by flash column chromatography, using a mixture of ethyl acetate and hexane. Both were recrystallized from heptane as white powders. The melting point of the trans-isomer was 156°–157° C., and that of the cis-isomer was 174°–175.5° C.

The cyclohexane bisphenols of this invention may be converted to polycarbonates by reaction with a carbonate source such as phosgene or dimethyl carbonate, using conventional techniques. These include melt polymerization, interfacial polymerization and interfacial conversion to bischloroformate followed by polymerization. Chain termination agents such as phenol may also be employed.

Such polycarbonates are another aspect of the invention; they comprise 1,3-bis(4-hydroxyphenyl)-1,3-dialkylcyclohexane structural units of the formula

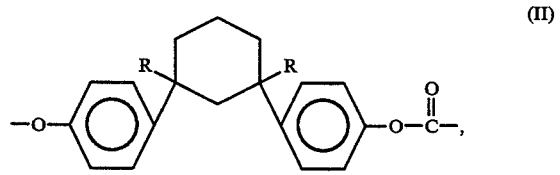

wherein R is as previously defined.

The polycarbonates of this invention include both homopolycarbonates and copolycarbonates. Copolycarbonates may include both cis- and trans-configured cyclohexane bisphenol structural units. They may also contain units corresponding to the dihydroxy compounds disclosed by name or formula (generic or specific) in U.S. Pat. No. 4,217,438, the disclosure of which is incorporated by reference herein. Such copolycarbonates typically comprise about 25–75% by number of cyclohexane bisphenol units (cis- or trans-isomer or both), with the balance being other units.

Said other units include those having the formula

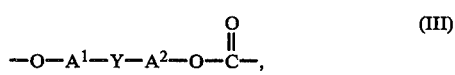

wherein each of $A^1$ and $A^2$ is a monocyclic divalent aromatic radical and Y is a bridging radical in which one or two atoms separate $A^1$ from $A^2$. The free valence bonds in formula III are usually in the meta or para positions of $A^1$ and $A^2$ in relation to Y.

The $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred units of formula III are 2,2-bis(4-phenylene)propane carbonate units, which are derived from bisphenol A and in which Y is isopropylidene and $A^1$ and $A^2$ are each p-phenylene.

The preparation of the polycarbonates of this invention is illustrated by the following examples. Molecular weights were determined by gel permeation chromatography relative to polystyrene.

EXAMPLES 2-5

Various bisphenol combinations in the amount of 11% w/v were combined with methylene chloride and with the following volume percentages of other materials, all percentages being based on said methylene chloride,:

Water—85%;
5% w/v triethylamine solution in methylene chloride—1.5%;
5% w/v phenol solution in methylene chloride—2.4%.

Phosgene was passed into the mixtures, with stirring, for 20 minutes to a total of 7% w/v, as the pH values of the aqueous phases were maintained between 10.5 and 11.5 by the addition of 25% aqueous sodium hydroxide solution. The mixtures were then purged with nitrogen for 15 minutes and the organic phases separated, washed twice with 3% aqueous hydrochloric acid solution and four times with water and dried over magnesium sulfate. The dried solutions were poured into methanol and the precipitated solids were redissolved in methylene chloride, precipitated by the addition of acetonitrile, redissolved again in methylene chloride and reprecipitated by the addition of methanol. The resulting copolycarbonates were dried to constant weight. Their identities and properties are listed in the following table.

| Example | Bisphenol, mole % | Mw | Mw/Mn | Tg. °C. |
| --- | --- | --- | --- | --- |
| 2 | Ex. 1 (trans), 82<br>Ex. 1 (cis), 18 | 69,500 | 2.11 | 192 |
| 3 | Ex. 1 (trans), 34<br>Bisphenol A, 66 | 131,300 | 3.29 | 174 |
| 4 | Ex. 1 (cis), 34<br>Bisphenol A, 66 | 81,300 | 3.20 | 162 |
| 5 | Ex. 1 (trans), 23.8<br>Ex. 1 (cis), 10.2<br>Bisphenol A, 66 | 119,700 | 3.40 | 171 |

Similar results were obtained with bisphenol solutions in methylene chloride as dilute as 2.5% w/v and triethylamine, phenol and pphosgene proportions as low as 0.75%, 0.80% and 5%, respectively.

What is claimed is:

1. A 1,3-bis(4-hydroxyphenyl)-1,3-dialkylcyclohexane of the formula

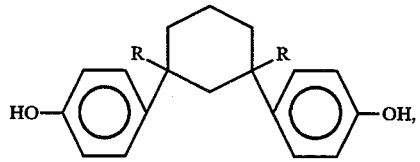

wherein R is a $C_{1-4}$ primary alkyl radical.

2. A 1,3-bis(4-hydroxyphenyl)-1,3-dialkylcyclohexane according to claim 1 wherein each R is methyl.

3. A 1,3-bis(4-hydroxyphenyl)-1,3-dialkylcyclohexane according to claim 1 in cis-configuration.

4. A 1,3-bis(4-hydroxyphenyl)-1,3-dialkylcyclohexane according to claim 1 in trans-configuration.

* * * * *